United States Patent [19]
Ehrhardt

[11] Patent Number: 4,859,431
[45] Date of Patent: Aug. 22, 1989

[54] RHENIUM GENERATOR SYSTEM AND ITS PREPARATION AND USE

[75] Inventor: Gary J. Ehrhardt, Columbia, Mo.

[73] Assignee: The Curators of the University of Missouri, Columbia, Mo.

[21] Appl. No.: 147,435

[22] Filed: Jan. 25, 1988

Related U.S. Application Data

[63] Continuation of Ser. No. 929,644, Nov. 10, 1986, abandoned.

[51] Int. Cl.$^4$ .................... C01G 47/00; C01G 41/00; G21G 1/00; A61K 43/00
[52] U.S. Cl. .......................................... 423/2; 423/49; 423/55; 423/58; 252/645; 376/158; 376/189; 250/432 PD; 424/1.1
[58] Field of Search ............... 423/2, 49, 58; 252/645; 250/432 PD; 376/186

[56] References Cited

U.S. PATENT DOCUMENTS

| | | | |
|---|---|---|---|
| 3,332,737 | 7/1967 | Kraus | 423/6 |
| 4,280,053 | 7/1981 | Evans | 423/2 X |
| 4,738,834 | 4/1988 | Moore et al. | 423/2 |

FOREIGN PATENT DOCUMENTS 3675278  4/1981  Australia .

OTHER PUBLICATIONS

J. Evans et al., Appl. Radiat. Isot., vol. 38, No. 1, pp. 19–29, 1987, Int. J. Radiat. Appl. Instrum., Part A.
W. Rieman and H. Walton, *Ion Exchange in Analytical Chemistry*, Chapter 8, pp. 140–142 and 144–145, Pergammon Press, Oxford, New York, 1970.
Blachot, J. et al., "Un Generateur de $^{188}$Re á Partir de $^{188}$W", International Journal of Applied Radiation and Isotopes, vol. 20, pp. 467–470, 1969.
Kordyukevich, V. O. et al., "Extractive Separation of Rhenium Isotopes Without Carriers from a Tungsten Target", Radiokhimya, vol. 26, No. 5, pp. 625–629, 1984.
Evans, J. V. et al., "A New Generator for Technetium-99m", purportedly presented at 3rd World Congress Nuclear Medicine & Biology, Paris, Aug. 1982.
Narasimhan, D. V. S. et al., "A New Method for $^{99m}$Tc Generator Preparation", J. Radioanal. Nucl. Chem., Letters 85, 6, pp. 345–355, 1984.
Narasimhan, D. V. S. et al., "Preparation of a Sterile Closed System $^{99m}$Tc Generator Based on Zirconium Molybdate", J. Radioanal. Nucl. Chem., Letters 85, 3, pp. 163–172, 1984.
Boyd, R. E., "Technetium-99m Generators-The Available Options", Int. J. Appl. Radiat. Isot., vol. 33, pp. 801–809, 1982.

*Primary Examiner*—Brooks H. Hunt
*Assistant Examiner*—Virginia B. Caress
*Attorney, Agent, or Firm*—Christensen, O'Connor, Johnson & Kindness

[57] ABSTRACT

A process for preparing a tungsten-188/rhenium-188 generator having a tungstate matrix containing W-188 produced by irradiating tungsten-186 in the tungstate compound. High activity, carrier-free rhenium-188 may be obtained by elution. Substrates for further purifying the rhenium-188 eluate are also described.

8 Claims, No Drawings

RHENIUM GENERATOR SYSTEM AND ITS PREPARATION AND USE

This application is a continuation application based on prior copending application Ser. No. 929,644, filed Nov. 10, 1986, Rhenium Generator System and its preparation and use, now abandoned.

FIELD OF THE INVENTION

This invention relates to the production of radionuclides useful for therapeutic and diagnostic medical applications, particularly to radionuclide generator systems, and more particularlly to tungsten-188/rhenium-188 generators.

BACKGROUND OF THE INVENTION

Radionuclides, meaning atomic species that exhibit radioactivity, are useful for diagnostic and therapeutic techniques such as tumor imaging and radiotherapy of tumors. Such techniques have increased the demand for available supplies of carrier-free radionuclides having reasonable half lives such as Technetium-99m (Tc-99m, half-life 6.02 hours) used for diagnostic purposes. One method of obtaining such radionuclides is via extraction of a "daughter" radionuclide which is a decay product of a longer-lived ("parent") radionuclide. For example, Tc-99m is the daughter radionuclide of molybdenum-99 (Mo-99, half-life 66.02 hrs).

Devices known as generators are commercially available to provide separation of a daughter radionuclide from its parent radionuclide to provide a supply of the relatively short-lived daughter isotope. The parent and daughter radionuclides may be separated using chromatographic, solvent extraction, or sublimation generators. The chromatographic generators, due to their simplicity and compact nature, are more convenient to use in hospitals and other institutions where radionuclides are used for diagnosis and therapy. For use in such generators, the parent radionuclide should have a sufficient long half-life to provide enough time for transit and storage prior to commencing the extraction procedure.

Chromatographic generators, such as those used to produce Tc-99m from Mo-99, typically contain insolubilized parent radionuclide adsorbed onto a bed or column of material such as aluminum oxide ("alumina") for which the daughter radionuclide has relatively little affinity. The daughter radionuclide, which forms from decay of the parent, is then periodically eluted from the column, for example using physiological saline. Typically, the daughter radionuclide product will be of high specific activity and is referred to as "carrier free" since it is produced by beta decay of a parent radionuclide, and the product is relatively free of stable isotopes of the daughter radionuclide.

Until recently, prior chromatographic generators were only able to provide high specific activity product radionuclides at relatively low concentrations from low specific activity (n,γ) parent radionuclides such as Mo-99 due to the necessity of using large quantities of alumina and eluting solution to obtain the daughter radionuclide. As a result, fission-produced parent radionuclides have been preferred for producing radionuclides such as Tc-99m. Unfortunately, fission-produced radionuclides require complex facilities and safety precautions that entail high costs relative to the amount of daughter radionuclide produced.

Recently, a chromatographic Mo-99/Tc-99m generator has been developed that employs a matrix composed of zirconium molybdate containing Mo-99. Evans et al., U.S. Pat. No. 4,280,053. This matrix is said to be essentiallyl non-elutable, and to allow the Tc-99m produced in the matrix to diffuse through and from the matrix during elution.

Another radionuclide which shows promise for therapeutic and diagnostic applications is Rhenium-188 (Re-188), a decay product of tungsten-188 (W-188), a low specific activity isotope produced from naturally occurring tungsten (W-186).

Although the chemical properties of rhenium ae not as well known as those of technetium, certain of its properties suggest it may be suited for use in radiotherapeutic applications, for example, as a label for conjugation to monoclonal antibodies for targeting to tumors. Re-188 (half-life 16.98 hours) has a longer half-life than Tc-99m (6.02 hours), possesses a strong particulate emission (beta energy of 2.12 MeV) (in contrast, Tc-99m has no particulate emission), and has an imageable gamma emission (15%, 155 keV) ideal for current gamma camera imaging of tumors. W-188 radionuclide is derived from either natural tungsten (W-186) or, preferably, from a target tungsten material enriched in W-186 by double neutron capture using a high-flux reactor. The nuclear properties of this isotopic system are as follows:

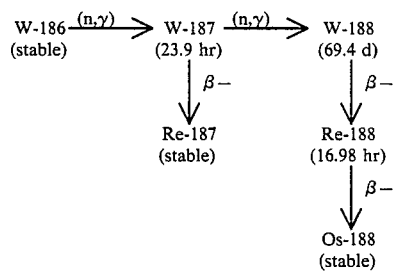

Previous tungsten/rhemium generators have consisted of small, alumina columns with relatively small amounts of tungsten targets adsorbed on the columns and, thus, low rhenium yields in the microcurie ($\mu$Ci) range. To increase the amount of rhenium obtainable from such columns, (i.e., in the millicurie range, mCi) larger column masses are necessary in order to contain larger amounts of target tungsten. These larger columns, in turn, require increased eluting volumes.

In addition, prior W-188/Re-188 generators using alumina columns have provided poor yields of Re-188 and unacceptable levels of release, or "breakthrough" of W-188 from the column due primarily to the necessity of adsorbing large (0.5–2.0 grams) amounts of target tungsten (primarily as W-186) onto the alumina column. A W-188/Re-188 generator system incorporating larger amounts of target tunsten to produce high yields (millicuries) of carrier-free Re-188 in small volumes (milliliters) without significant W-188 contamination, would be useful for therapeutic and diagnostic applications.

SUMMARY OF THE INVENTION

Accordingly, the present invention provides a process for preparing a tungsten-188/rhenium-188 generator employing a tungstate generator matrix containing low specific activity W-188 produced by irradiating W-186. The matrix may be placed in an elutable container, such as a column, for harvesting substantially carrier-free, high specific activity Re-188. The process for preparing the generator matrix, composed of tungsten trioxide and zirconium, includes dissolving irradiated tungsten trioxide in a heated basic solution and adding this solution to an acidic zirconium-containing solution to form an acidic slurry in which a zirconyl tungstate precipitate forms. The slurry is neutralized using a basic solution. W-188 radionuclide produced by irradiation is contained within the precipitate used to form the generator matrix. Rhenium-188 may be recovered by eluting the generator matrix with a saline solution, and the eluate may be further purified using an alumina or zirconium oxide substrate.

DETAILED DESCRIPTION

The present invention provides a process for preparing a W-188/Re-188 generator in the form of a substantially insoluble matrix containing W-188 which is permeable to diffusion of Re-188 in the form of the perrhenate ion ($ReO_4^-$). The matrix is preferably composed of a W-186 tungsten-containing material, such as a tungstate compound, which is irradiated to form relatively low specific activity W-188. The resulting parent radionuclide material is then dissolved in a heated basic solution, which is then combined with an acidic zirconium solution to precipitate the zirconyl tungstate matrix. The matrix, which contains the parent radionuclide W-188, may then be placed in a container for harvesting the desired high specific activity daughter radionuclide Re-188 by elution. Details of the preparation of the generator matrix and its use are described below.

The substantially insoluble precipitate containing the parent radionuclide, W-188, is prepared for use in forming a permeable matrix which allows a high rate of diffusion of the daughter radionuclide ion ($ReO_4^-$) generated as a decay product of the parent. Through this procedure, the Re-188 is produced in high yield and at a relatively high specific activity using simple elution methods, without requiring large beds or columns and hus the large elution volumes of prior methods. Tungsten (W) in the form of a tungstate compound, such as tungsten-186 trioxide ($WO_3$), when suitably combined with a soluble salt of a metallic cation, such as zirconyl ($ZrO^{+2}$) to form a precipitate, provides a matrix that is highly insoluble in solutions such as physiological saline used to elute chromatographic generators.

The tungstate compound is irradiated at high neutron flux levels using, for example, a 10 megawatt nuclear reactor to produce W-188, the parent radionuclide. Since tungsten trioxide is unstable in acid, to form the tungstate precipitate the irradiated tungsten trioxide is preferably initially dissolved in a basic solution with a hydroxyl concentration ($[OH^-]$) of from 2 to 10 moles/liter. The base may be sodium hydroxide, potassium hydroxide, ammonium hydroxide or a similar source of hydroxyl ion. Preferably, the basic solution has been heated to a temperature in the range of 50° C. to 60° C. to dissolve the tungsten trioxide. The resulting solution may then be cooled to room temperature and combined with an acidic aqueous solution, such as hydrochloric acid (HCl), nitric acid ($HNO_3$) or sulfuric acid ($H_2SO_4$) with a hydrogen ion concentration ($[H^+]$) of from 1 to 6 moles/liter and preferably from 4 to 5 moles/liter, and containing zirconyl ion. It was found that when the basic and acidic solutions were combined at temperatures in the range of from approximately 5° C. to 60° C., for each solution, precipitation of zirconyl tungstate still occurred.

The pH of the acidic and basic solutions are selected to produce a final slurry which remains acidic (pH 0 to 1) after the addition of the basic tungsten solution. It is preferable to slowly add the basic tungsten solution to the acid solution and not the acidic to the basic solution, to promote formation of zirconyl tungstate. This is because of the tendency of the zirconyl cation to form zirconium hydroxide, which reaction competes with the reaction of zirconyl cation and tungsten, potentially reducing the amount of zirconyl tungstate formed. In addition, because a certain amount of zirconium hydroxide will tend to form in the base of the combined solutions, a slight excess (preferably from 25% to 50%) of zirconium may be used to ensure formation of a zirconyl tungstate precipitate containing a 1:1 ratio of zirconium to total tungsten, thus compensating for the loss of some zirconyl to zirconium hydroxide. After precipitation, the slurry is adjusted to a pH of from 5 to 7, and preferably a pH of 7, using a base such as sodium hydroxide (NaOH) to prevent redissolving of the zirconyl tungstate. Any zirconium hydroxide which forms from the excess zirconyl cation used as described above, may precipitate when the slurry is adjusted to a basic pH. This precipitate may remain associated with the matrix and adsorb any solubilized tungsten released from the matrix which would otherwise contaminate the eluate.

The slurry is centrifuged and the precipitate is washed several times using deionized water or physiological saline and is filtered to remove any soluble tungsten (W-186 and W-188) not initially precipitated and, then, preferably, the precipitate is slowly air dried to remove excess liquid at room temperature. Alternatively, the precipitate may be oven dried, for example, at 100° C. The resulting glassy material which remains hydrated, is broken up, for example using a spatula or by sonication to form the generator matrix material. The matrix material may be transferred to an empty container for eluting and harvesting of the daughter product Re-188. Suitable containers may include, for example, a glass column such as those used in standard chromatography which is then encased in a "shell" including appropriate lead shielding, associated plumbing and a reservoir of eluant, to form a generator assembly. Alternatively, a separate, sterile reservoir may be supplied for each series of elutions. It is desirable to keep the matrix hydrated at all times. Periodically, the daughter Re-188 is conveniently eluted from the column using eluant solutions, such as saline, for example sodium chloride (NaCl) or sodium sulfate ($Na_2SO_4$). Physiological saline, preferably with a molarity of 0.15, is a preferred eluant solution.

Performance of the rhenium generator of the present invention may be expressed as elution efficiency. Elution efficiency may be calculated by measuring the amount of radioactivity of Re-188 present in the eluant divided by the amount of radioactivity of Re-188 originally present on the generator column, immediately prior to elution. The radioactivity of the Re-188 may be determined using standard instruments for measuring radioactivity including gamma ray spectrophotometers such as germanium detectors and sodium iodide scintillation spectrophotometers, which are capable of measuring low levels of radioactivity, or dose calibrators that can measure high levels of radioactivity. In the present invention, since the generator consists of a small column, the entire column may be placed in a dose calibrator to directly measure the radioactivity of Re-188 on the column before elution, and by subtracting from the value the amount of radioactivity of Re-188 on the column after elution, the amount of radioactivity of the Re-188 present in the eluant may be determined. This procedure provides a close approximation of the Re-188 present in the eluant because, at the appropriate setting on the dose calibrator, the radioactivity measured on the column may be attributed to Re-188. Elution efficiencies are typically measured after approximately 3 to 10 Re-188 halflives. Elution efficiencies of Re-188 as high as 55%–65% have been obtained using the generators of the present invention, which concentrations of Re-188 in the eluant of up to 4 mCi/ml and higher, determined immediately after elution and typically after 3 or 4 half-lives.

The radiochemical purity of Re-188 may be assessed using ion exchange reversed phase high-performance liquid chromatography (HPLC) or scintillator chromatography using nonradioactive perrhenate as a standard.

While zirconyl tungstate ($ZrOWO_4$), or $ZrOWO_4 \cdot XH_2O$ when hydrated, is the preferred compound for forming the matrices used to generate Re-188 in the present invention, other suitable matrices include tungstate compounds containing hafnium, titanium, cerium, iron, tin and barium, and mixtures of these compounds.

During the elution process, a certain amount of W-188 and W-186 in the eluant may be released from the matrix, for example, in the form of small particles of the zirconyl tungstate matrix, causing contamination of the Re-188. A porous glass or plastic structure, such as a fritted glass disc used in chromatography columns, may be used to retain some of these particles to prevent entry of tungsten into the eluate. However, the amount of W-188 released from the column is relatively low using the process of this invention (as low as 0.01%). This is because, in the present invention, a large fraction of the generator matrix would have to dissolve before a substantial fraction of the W-188 contained in it is released. Using the generator of the present invention, Re-188 may be eluted with less than 0.01% (of the total W-188 present on the column) breakthrough of W-188. Moreover, the level of W-188 present in the eluate may be reduced by several orders of magnitude using a substrate which is capable of adsorbing tungsten including W-188, such as an alumina column or zirconium hydroxide bed, to purify the solution eluted from the zirconyl tungstate matrix. Thus, the generator system of the present invention may include a second eluatable container, such as a chromatographic column enclosing a second matrix containing such a tungsten-specific matrix, for removing any released W-188, in addition to the container enclosing the generator matrix. Alternatively, the substrate which is capable of adsorbing tungsten may be incorporated into the generator column, for example, below the zirconyl tungstate matrix, so that the eluant passes through the substrate after first flowing through the zirconyl tungstate matrix. An additional advantage of the use of the tungsten-adsorbing substrate is that the loss of small particles of matrix may be minimized, which in turn decreases the amount of eluted fluid containing such contaminating particles which must be disposed of.

W-188/Re-188 generator devices made according to the present invention are quite compact and may be made using small masses of generator matrix. Since the W-188 can be produced at a specific activity of approximately 1 Curie (Ci)/gram or higher by neutron capture, it is apparent that small (Curie size) generator columns containing volumes as low as 5 ml may be constructed using this process.

The following Example is presented to illustrate the advantages of the present invention and to assist one of ordinary skill in making and using the same. The Example is not intended in any way to otherwise limit the scope of the disclosure or the protection granted by Letters Patent hereon.

EXAMPLE 1

Preparation of W-188

116 mg of isotopically enriched W-186 in the form of tungsten trioxide (Oak Ridge National Laboratories, Oak Ridge, Tennessee) was neutronirradiated at $3 \times 10^{14}$ neutrons/cm$^2$/sec for four to five months using the Missouri University Research Reactor to produce approximately 60 mCi of W-188 in the 116 mg of tungsten trioxide.

Preparation of Zirconyl-Tungstate Precipitate 116 mg of tungsten trioxide, irradiated as described above after decaying four months to a total activity of approximately 14 mCi, was added to 134 mg of non-irradiated $WO_3$ to equal 250 mg of $WO_3$, which was dissolved in 5 ml of 5M sodium hydroxide (NaOH) heated to 60° C. The resulting basic tungsten trioxide solution was allowed to cool to room temperature, and then slowly added to an acidic solution, approximately 7.5 ml of 4M HCl (to provide an excess of acid in the final solution) and containing 0.45 grams of zirconium nitrate (approximately 25% excess zirconium to ensure precipitation). The final slurry had a pH of 0 to 1 after addition of the basic tungsten solution. A white zirconyl tungstate precipitate formed immediately upon stirring and was neutralized using NaOH to a pH in the range of approximately 5 to 7 to prevent redissolving of the precipitate. The precipitate was then isolated by filtration and washed with physiological saline (0.9% NaCl) and then slowly dried at 25° C. The resulting glassy-white material was broken up using a spatula and transferred to an empty glass column (approximate volume 5–7 ml), containing a fritted glass disc (Mallinckrodt, Inc., St. Louis, MO). In the column, the matrix was again washed using physiological saline to release and remove any small particles from the matrix, to prevent entry of tungsten into the eluate, i.e., to reduce breakthrough. Water may also be used to wash the column.

W-188 was found to comprise less than 0.003% of the generator matrix, as determined from the radioactivity (mCi) of W-188 as measured using a dose calibrator.

Rhenium Generator

The above generator matrix column was fitted within a conventional housing of lead shielding, also containing an eluant reservoir and associated plumbing. Prior to the initial elution, the column was again washed using approximately 500 ml of physiological saline, to further reduce breakthrough from the matrix. Re-188 was then allowed to generate from approximately 7 mCi of W-188 within the column for 1 to 2 days after which the Re-188 was eluted using 5 to 10 ml of physiological saline. 4 mCi of Re-188 in the form of $ReO_4^-$ was obtained in the initial elution using the above procedure. Subsequently, 2 to 4 mCi of Re-188 was obtained from each elution over a three-week time period, using a single elution every other day.

The concentration profile (mCi/ml of eluate) of Re-188 obtained from the generator may be determined by measuring the radioactivity of the Re-188 obtained in a given volume of eluate for several elutions. These measurements may be compared to the total amount of radioactivity of the Re-188 generated on the column to determine at what timepoint in elution the highest activity of Re-188 is obtained. In addition, the specific activity of Re-188 obtained from the column may be measured by determining the total radioactivity of Re-188 present in the eluate from the column.

Elution Purity

To determine the amount of W-188 released from the matrix, eluates obtained as described above were analyzed using a multichannel analyzer (Nuclear Data, Inc., Schaumburg, IL) which showed that the W-188 content of the Re-188 solutions was between 0.008–0.01% of total activity on the column. The amount of breakthrough of W-188 was further reduced by passage over an alumina column or hydrous zirconium oxide adsorbent bed. No other significant radionuclide impurities were present.

Nonradioactive chemical impurities such as metals present in the eluates may be examined using atomic absorption of elutions.

Radiochemical Purity of Re-188

Perrhenate was the only material detected on an HPLC column after elution of the W-188/Re-188 generators described above.

Generator Performance

Generator performance was measured in terms of elution efficiency as described above using a sodium iodide spectrophotometer and a dose calibrator. Generator efficiencies were found to be from 55% to 65%.

The generator described herein may be made to hold from several hundred milligrams up to 1 gram of target tungsten trioxide to provide daughter Re-188 yields of several hundred millicuries.

Reusability of Generator

The generator prepared as described above was eluted regularly every other day for 2 to 3 weeks producing an average elution yield of 59%. Other W-188/Re-188 generators made according to the process described herein were found to give similarly consistent high yields over several months' time. This demonstrates that generators as described herein have a useful lifetime for production of Re-188.

The present invention avoids the need to use a high specific activity parent radionuclide produced from fission. Since W-188 is unlikely to be available carrier-free in the foreseeable future, the present invention, which uses W-188 produced from W-186, provides a convenient means for obtaining carrier-free Re-188 in useful quantities without requiring large columns which are difficult to shield and which require large volumes of eluate to obtain acceptable amounts of product. Previous smaller Re-188 generators could not hold enough adsorbed W-188 and attempts to increase the generator activity reduced the elution yield of Re-188 and increased release of W-188 from the column.

The Re-188 produced by the generator device described herein may be conjugated to antibodies, for example, those that recognize tumor-associated antigens, for radiotherapy or diagnostic purposes. In addition, the relatively long half-life or W-188 (69.4 days), and ready transportability of the generator matrix in columns or other containing devices, facilitates commercial supply and storage of the generator matrices produced according to the present invention.

While the present invention has been described in conjunction with the preferred emodiments, one of ordinary skill after reading the foregoing specification will be able to effect various changes, substitutions of equivalents and alterations to the methods and compositions set forth herein. It is therefore intended that the protection granted by Letters Patent hereon be limited only by the appended claims and equivalents thereof.

The embodiments of the invention in which an exclusive property or privilege is claimed are defined as follows:

1. A process for preparing a radionuclide generator useful for producing Re-188, comprising the steps:
    (a) reacting a basic tungstate solution containing W-188 with an acidic solution containing zirconyl ion to form a zirconyl tungstate precipitate containing W-188; and,
    (b) disposing said zirconyl tungstate precipitate in an elutable container.

2. A process for preparing rhenium-188 comprising the step of eluting rhenium-188 from a matrix consisting essentially of a tungstate precipitate comprising tungsten-188.

3. The process of claim 2, wherein said tungstate precipitate comprises zirconyl tungstate.

4. The process of claim 2, wherein said matrix is prepared by reacting a basic tungstate solution containing W-188 with an acidic solution containing a zirconyl ion to form a zirconyl precipitate containing W-188.

5. A Re-188 generator comprising an eluatble container defining an eluant flow path, said container containing a first matrix comprising a subtantially non-elutable tungstate compound containing W-188 and a second matrix comprising a tungsten-188 specific substrate, said first and second matrices being disposed in said flow path to sequentially contact eluant with the first matrix and then the second matrix.

6. A radionuclide generator for producing rhenium-188 comprising a substantially insoluble matrix consisting essentially of a tungstate compound containing tungsten-188, said matrix being permeable to fluid passage and permitting diffusion of rhenium-188 therethrough.

7. The radionuclide generator of claim 1, wherein said matrix consists essentially of zirconyl tungstate containing tungsten-188.

8. The radionuclide generator of claim 1, wherein said matrix is prepared by reacting a basic tungstate solution containing W-188 with an acidic solution containing a zirconyl ion to form a zirconyl precipitate containing W-188.

* * * * *

UNITED STATES PATENT AND TRADEMARK OFFICE
CERTIFICATE OF CORRECTION

PATENT NO. : 4,859,431

DATED : August 22, 1989

INVENTOR(S) : G. Ehrhardt

It is certified that error appears in the above-identified patent and that said Letters Patent is hereby corrected as shown below:

Column 1, line 14, "particularlly" should be --particularly--
Column 1, line 41, "sufficient" should be --sufficiently--
Column 2, lines 4 & 5, "essentiallyl" should be --essentially--
Column 2, line 42, "rhemium" should be --rhenium--
Column 3, line 29, "W-188,may" should be --W-188, may--
Column 3, line 41, "hus" should be --Thus--
Column 4, line 50, "conveiently" should be --conveniently--
Column 5, line 3, "the" should be --this--
Column 5, line 46, "magitude" should be --magnitude--
Column 6, line 4, "contaning" should be --containing--
Column 8, line 11, "emodiments" should be --embodiments--
Column 8, line 41 (Claim 5, line 3), "subtantially" should be --substantially--
Column 8, line 53 (Claim 7, line 1), "Claim 1" should be --Claim 6--
Column 8, line 56 (Claim 8, line 1), "Claim 1" should be --Claim 6--

Signed and Sealed this

Twenty-fifth Day of September, 1990

Attest:

HARRY F. MANBECK, JR.

Attesting Officer

Commissioner of Patents and Trademarks